(12) United States Patent
Fukuhara

(10) Patent No.: US 10,209,182 B2
(45) Date of Patent: Feb. 19, 2019

(54) IMAGE-FORMING APPARATUS THAT ACQUIRES PASSAGE TIMES OF COLOR DEVELOPERS

(71) Applicant: CANON KABUSHIKI KAISHA, Tokyo (JP)

(72) Inventor: Takashi Fukuhara, Higashikurume (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/730,074

(22) Filed: Oct. 11, 2017

(65) Prior Publication Data

US 2018/0106722 A1 Apr. 19, 2018

(30) Foreign Application Priority Data

Oct. 17, 2016 (JP) .................................. 2016-203609

(51) Int. Cl.
*G03G 15/08* (2006.01)
*G01N 21/47* (2006.01)
*G01N 21/55* (2014.01)
*G03G 15/01* (2006.01)

(52) U.S. Cl.
CPC ......... *G01N 21/4738* (2013.01); *G01N 21/55* (2013.01); *G03G 15/0121* (2013.01); *G03G 2215/00616* (2013.01)

(58) Field of Classification Search
CPC ................................................ G01N 21/4738
USPC .......................................................... 399/74
See application file for complete search history.

(56) References Cited

FOREIGN PATENT DOCUMENTS

| JP | H06155817 A | 6/1994 |
|---|---|---|
| JP | 2002040743 A | 2/2002 |
| JP | 5094308 B2 | 12/2012 |

OTHER PUBLICATIONS

Computer translation of reference JP2009-080246A to Shinichi on Apr. 9, 2015.*
Office Action issued in Japanese Appln. No. 2016-203609 dated Oct. 16, 2018. English translation provided.

* cited by examiner

*Primary Examiner* — Quana M Grainger
(74) *Attorney, Agent, or Firm* — Rossi, Kimms & McDowell LLP

(57) ABSTRACT

The image-forming apparatus includes multiple developing units that form images using multiple color developers, an image carrier that, in color displacement detection, carries the developers transferred thereon at mutually different image-carrying positions, an optical sensor that projects a light to the image carrier and receives a reflected light from the image carrier, and an acquirer that acquires, in response to output from the optical sensor, passage times at which the developers on the image carrier respectively pass a detection position. The optical sensor receives a diffusively reflected light from a non-transferred area of the image carrier on which the developers are not transferred. The acquirer acquires the passage times of all the developers, in response to changes in the output from the optical sensor at an output level higher than that corresponding to a diffusively reflected light from the developers on the image carrier.

10 Claims, 7 Drawing Sheets

IMAGE-FORMING APPARATUS THAT ACQUIRES PASSAGE TIMES OF COLOR DEVELOPERS

BACKGROUND OF THE INVENTION

Field of the Invention

The present invention relates to a color image-forming apparatus such as a color laser printer and a color copier.

Description of the Related Art

A tandem type color image-forming apparatus detects a color displacement using multiple color displacement detection images (patches) formed on an intermediate transferring belt as an image carrier by multiple color toners (developers), and using an optical sensor that detects a light projected to a predetermined position on the intermediate transferring belt and reflected thereby. Specifically, the apparatus forms, on the intermediate transferring belt, the multiple color patches using a reference color toner and a comparative color toner at a predetermined interval. The optical sensor receives a specularly reflected light from an area where no patch is formed on the intermediate transferring belt, and detects a passage time of each color toner at which each patch passes a predetermined position in response to attenuation of a received light amount (detection signal). Then, the apparatus calculates the color displacement amount from a difference of the passage time of the reference color toner from that of the comparative color toner.

However, a deterioration of the intermediate transferring belt with use of the apparatus decreases its specular reflectance, which decreases a contrast of the detection signal output from the optical sensor. Thereby, detection accuracy of the passage time of each color toner may decrease.

Japanese Patent No. 5094308 discloses an image-forming apparatus that compares a change in specularly reflected light amount from the intermediate transferring belt with a change in diffusively reflected light amount from a chromatic color toner whose diffusive reflectance is high, and acquires, as a passage time, a time at which one of the reflected light amount changes is larger than the other. The image-forming apparatus disclosed in Japanese Patent No. 5094308 uses the diffusively reflected light for detecting the passage time of the chromatic color toner and, on the other hand, uses a specularly reflected light from an achromatic color (black) toner because its diffuse reflectance is small. Thus, the optical sensor has two detectors that are a detector for detecting the specularly reflected light from the intermediate transferring belt and another detector for detecting the diffusively reflected light therefrom.

However, an optical axial displacement between the two detectors in this apparatus configuration causes a difference in detection positions of the chromatic and achromatic color toners, which causes a detection error of the passage time of each color toner. Furthermore, a change in surface inclination of the intermediate transferring belt changes a light ray angle of the specularly reflected light, which varies the passage time of the achromatic color toner relative to that detected for the diffusely reflected light on which an influence of the surface inclination of the intermediate transferring belt is small. These make it difficult to detect the color displacement with high accuracy.

SUMMARY OF THE INVENTION

The present invention provides an image-forming apparatus capable of detecting a passage time of each color toner with high accuracy without being influenced by an optical axial displacement between multiple detectors provided in an optical sensor and by a change in light ray angle of a specularly reflected light from an image carrier.

The present invention provides as an aspect thereof an image-forming apparatus including multiple developing units configured to form images using multiple color developers whose colors are mutually different, an image carrier configured to, in color displacement detection, carry the multiple color developers transferred thereon from the multiple developing units at mutually different image-carrying positions, an optical sensor configured to project a light to the image carrier and receive a reflected light from the image carrier, and an acquirer configured to acquire, in response to output from the optical sensor, passage times at which the multiple color developers carried by the image carrier respectively pass a detection position. The optical sensor is configured to receive a diffusively reflected light from a non-transferred area of the image carrier on which the developers are not transferred, and the acquirer is configured to acquire the passage times of all the multiple color developers, in response to changes in the output from the optical sensor at an output level higher than that corresponding to a diffusively reflected light from the developers on the image carrier.

The present invention provides as another aspect thereof a non-transitory storage medium storing a computer program for causing a computer in the above image-forming apparatus to execute the above process.

Further features of the present invention will become apparent from the following description of exemplary embodiments with reference to the attached drawings.

DESCRIPTION OF THE EMBODIMENTS

Exemplary embodiments of the present invention will hereinafter be described with reference to the accompanying drawings.

Figure 1:
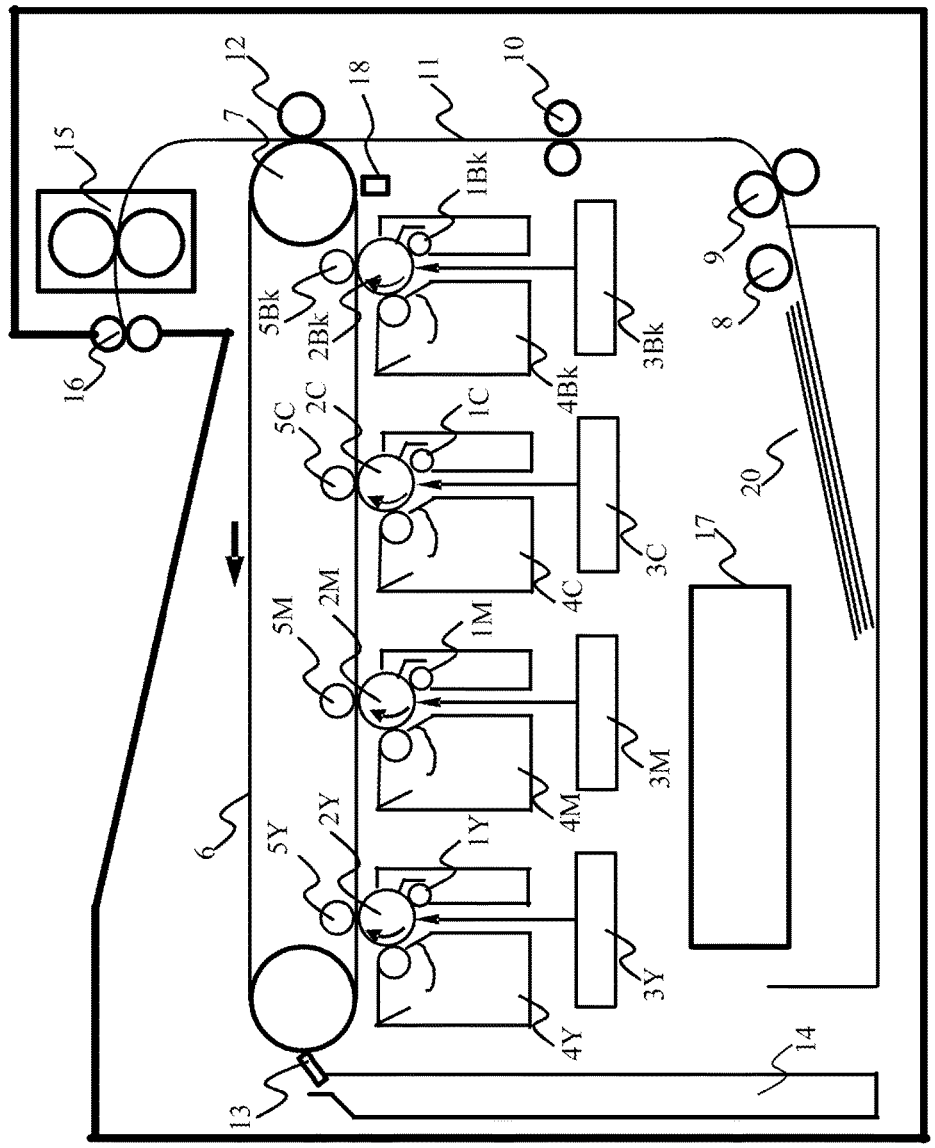
FIG. 1 illustrates a configuration of an image-forming apparatus that is an embodiment of the present invention.

First, description will be made of an embodiment of an image-forming apparatus common to Embodiments 1 and 2 described later. In FIG. 1, reference characters Y, M, C and Bk added to ends of part of reference numerals mean that constituent elements denoted by those reference numerals and characters correspond respectively to yellow, magenta, cyan and black, which are colors of toners as developers. However, in the following description of the constituent elements for the respective colors, the Y, M, C and Bk are not added to the reference numerals.

A charging unit 1 for each color evenly charges a photoconductive drum 2 for each color. The photoconductive drum 2 is rotationally driven in a direction indicated by a thin arrow in FIG. 1. An exposing unit 3 for each color projects a laser light to the corresponding photoconductive drum 2 to form thereon an electrostatic latent image.

A developing controller 4 applies a developing bias voltage to the photoconductive drum 2 to supply a toner to the electrostatic latent image, thereby forming a toner image as a visible image on the photoconductive drum 2. The developing controller 4 and the photoconductive drum 2 constitute a developing unit.

A primary transferring roller 5 for each color to which a primary transferring bias voltage is applied transfers each toner image on the photoconductive drum 2 for each color to an intermediate transferring belt 6 that is an image carrier. The intermediate transferring belt 6 is rotationally driven in a bold arrow direction by a driving roller 7. The photoconductive drums 2 for the respective colors transfer the toner images formed thereon to the same intermediate transferring belt 6 such that the transferred toner images overlap each other, thereby forming a color image.

Carrying rollers 8, 9 and 10 carry a recording sheet stored in a cassette 20 to a secondary transferring roller 12 along a carrying path 11. The secondary transferring roller 12 to which a primary transferring bias voltage is applied transfers the toner image (color image) formed on the intermediate transferring belt 6 to the recording sheet. A remaining toner not transferred to the recording sheet is removed from the intermediate transferring belt 6 by a cleaning blade 13 and is collected into a removed toner collection container 14. The recording sheet to which the toner image has been transferred is heated and pressed by a fixing unit 15, and thereby the toner image is fixed to the recording sheet. Then, the recording sheet is ejected to outside the apparatus by a carrying roller 16.

An engine controller 17 includes a microcomputer and performs various drive controls for driving the image-forming apparatus and controls using sensors. At a position facing a portion of the intermediate transferring belt 6 wounded on the driving roller 7, a color displacement sensor 18 as an optical sensor is provided. In this embodiment, the intermediate transferring belt 6 has light diffusivity.

Figure 2A:
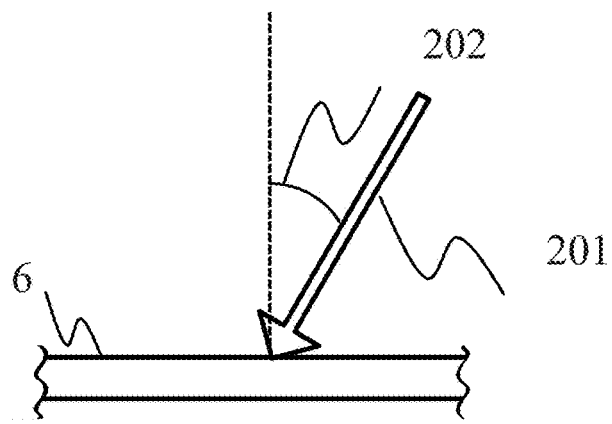
FIGS. 2A and 2B illustrate an incident angle dependency of a reflected light from an image carrier in this embodiment.
Figure 2B:
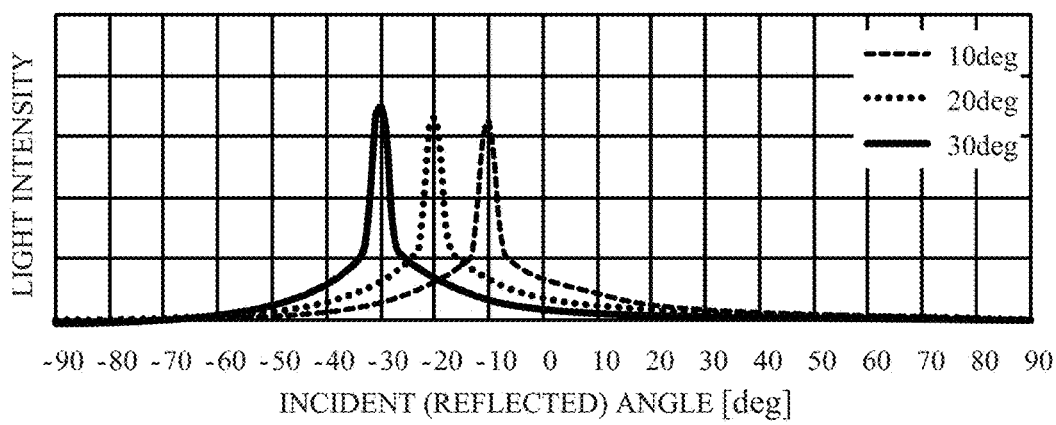

With reference to FIGS. 2A and 2B, description will be made of an example of an incident angle dependency of a light projected from the color displacement sensor 18 onto this intermediate transferring belt 6 and reflected thereby. FIG. 2A illustrates an angular relation between the intermediate transferring belt 6 and an incident angle 202 of light rays 201 thereto. FIG. 2B illustrates an incident angle dependency, for various incident angles 202, of the reflected light rays from the intermediate transferring belt 6 having a comparatively even light diffusivity. Graphs of a broken line, a dotted line and a solid line respectively indicate reflected light intensity distributions when the incident angles 202 are 10 degree, 20 degree and 30 degree.

For example, when the incident angle 202 to the intermediate transferring belt 6 is 30 degree, a reflected light intensity distribution is generated by light diffusion in a range of ±30 degrees centering on a specular reflection angle of −30 degree at which the reflected light rays have a peak intensity. Also, when the incident angles 202 to the intermediate transferring belt 6 are 10 degree and 20 degree, reflected light intensity distributions are respectively generated by light diffusion in ranges of ±30 degrees centering on specular reflection angles of −10 degree and −20 degree at which the reflected light rays have a peak intensity. Such a property of the intermediate transferring belt 6 is called a forward scattering property.

The intermediate transferring belt 6 having the property illustrated in FIG. 2B includes two layers that are a surface layer and a base layer. In the surface layer, dispersed electrical conductive particles and surface-layer particles for improving a secondary transfer property are added into a heat or ultraviolet curable resin. In the base layer (light diffusive layer), an electric resistance adjuster such as carbon black is dispersed. Changing an additive amount of the electric resistance adjuster can adjust a light absorption amount inside the intermediate transferring belt 6, thereby increasing or decreasing an amount of the diffusively reflected light radiating outside the intermediate transferring belt 6.

As other examples, transferring minute concavo-convex shapes of a molding to the base layer in manufacturing the intermediate transferring belt 6 or forming minute concavo-convex shapes on a surface of the surface layer in a post process makes it possible to provide to the base layer a diffusive reflection property.

These are examples of the intermediate transferring belt 6 in this embodiment. However, it is only necessary for the intermediate transferring belt 6 to satisfy a condition that an amount of a diffusively reflected light from a non-transferred area where any toner is not transferred is larger than that from each color toner.

Figure 3A:
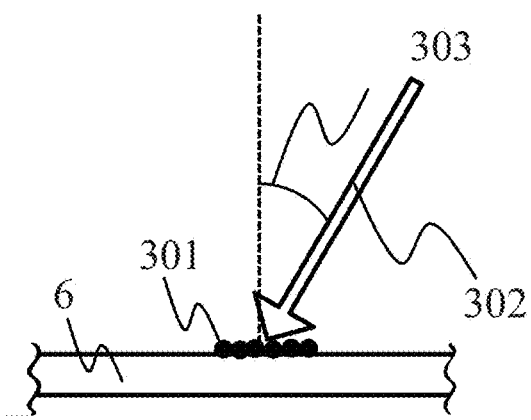
FIGS. 3A to 3C illustrate an incident angle dependency of a reflected light from a developer in this embodiment.
Figure 3B:
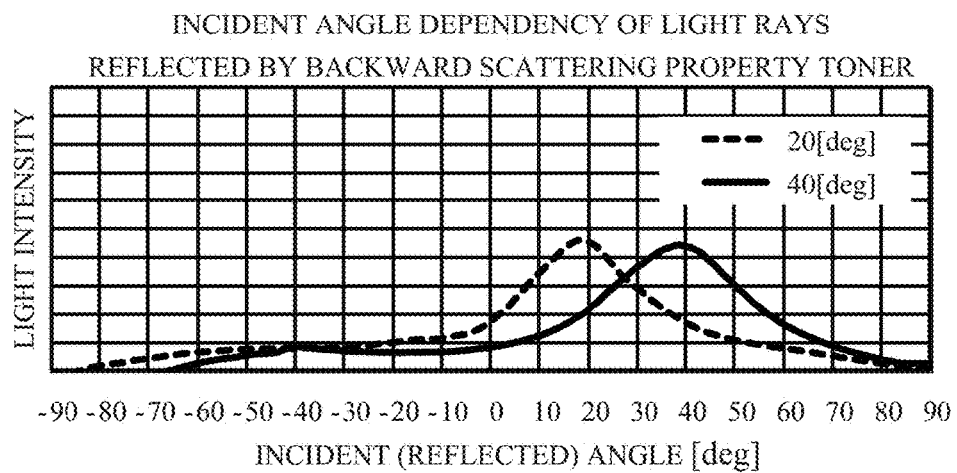

Next, with reference to FIGS. 3A to 3C, description will be made of an incident angle dependency of a light projected from the color displacement sensor onto a toner and reflected thereby. FIG. 3A illustrates an angular relation between a toner 301 transferred to the intermediate transferring belt 6 and an incident angle of light rays 302 to the toner 301. FIG. 3B illustrates an incident angle dependency of the reflected light rays from the toner 301 having a backward scattering property. Graphs of a broken line and a solid line respectively indicate reflected light intensity distributions when the incident angles 303 are 20 degree and 30 degree.

For example, when the incident angle to the toner 301 is 40 degree, the reflected light rays indicate a light scattering property in which a peak intensity exists at a reflection angle of 40 degree equal to the incident angle and the reflected light rays are distributed in a comparatively broad angular range. Also when the incident angle to the toner 301 is 20 degree, the reflected light rays have a peak intensity at a reflection angle of 20 degree equal to the incident angle and are distributed in a comparatively broad angular range. Such a property of the toner 301 is called a backward scattering property. A specific example of this toner 301 is a toner, such as a polymerized toner, that includes toner particles having approximately uniform shapes.

Figure 3C:
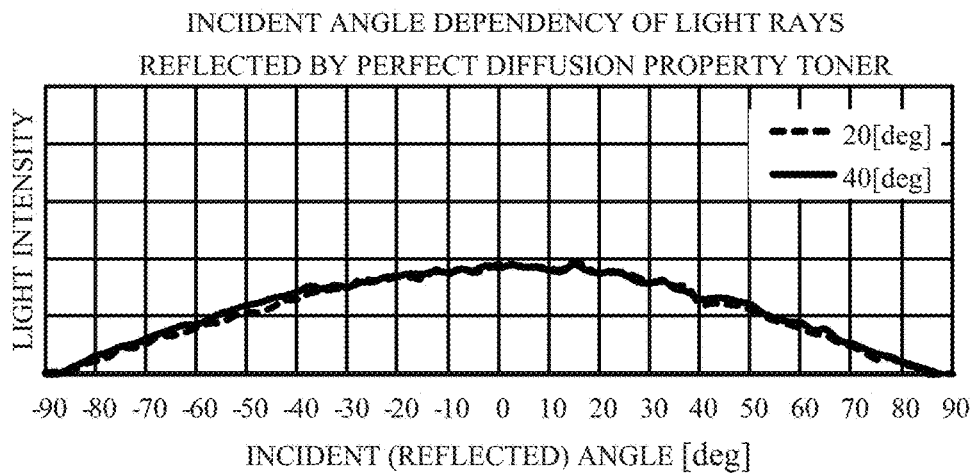

FIG. 3C illustrates an incident angle dependency of the reflected light rays when the toner 301 has a perfect diffusion property. Graphs of a broken line and a solid line respectively indicate reflected light intensity distributions when the incident angles 303 are 20 degree and 30 degree. For example, when the incident angle to the toner 301 is 40 degree, the reflected light rays indicate a light scattering property in which the reflected light rays are distributed in a broad angular range. Similarly, when the incident angle to the toner 301 is 20 degree, the reflected light rays indicate a light scattering property in which the reflected light rays are distributed in a broad angular range. As just described, the toner 301 has the perfect diffusion property that does not depend on the light ray's incident angle. As a specific example of such a toner 301, there is a toner including toner particles produced so as not to have uniform diameters and shapes, that is, to have various particle diameters and shapes.

Next, description will be made of configuration examples of the color displacement sensor 18 (405 and 505) and methods of detecting passage times of the toners (each hereinafter referred to as "a passage time point of each toner" or "a toner passage time point"). The detection of the toner passage time points is performed in color displacement detection between the mutually different color toners, that is, in a state where a color displacement detection mode is set.

Embodiment 1

Figure 4:
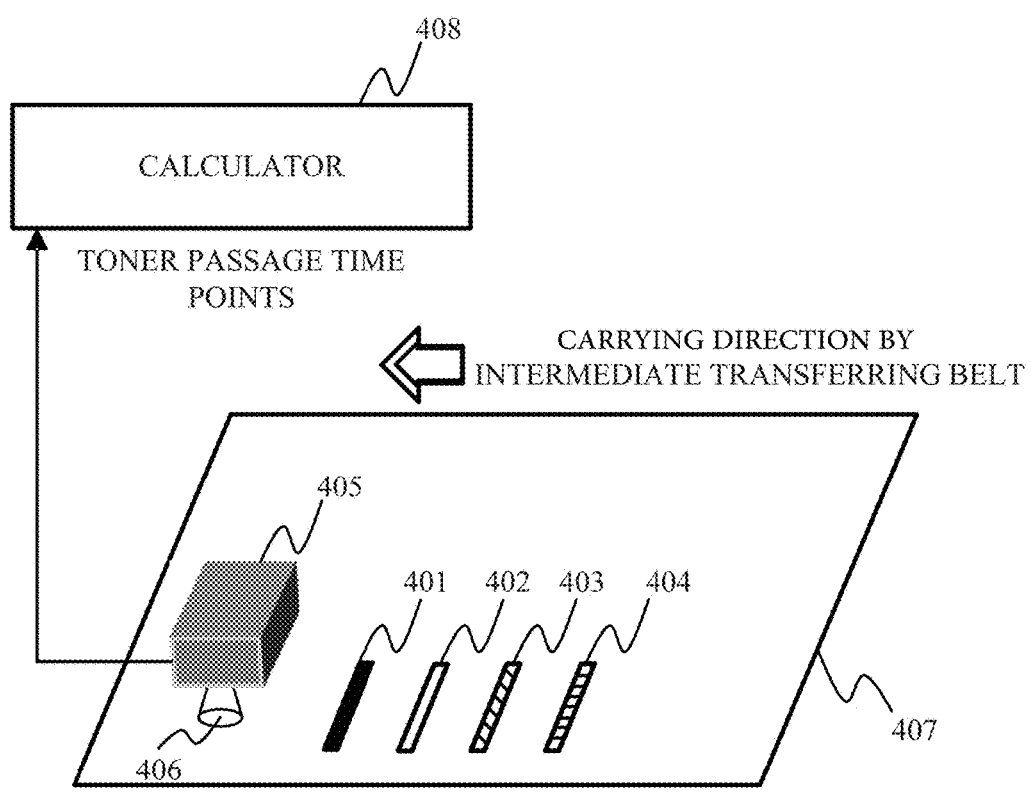
FIG. 4 illustrates a configuration for detecting a color displacement in Embodiment 1.

A first embodiment (Embodiment 1) will describe a case where the intermediate transferring belt 6 has the forward scattering property illustrated in FIG. 2B and the toner is a polymerized toner having the backward scattering property illustrated in FIG. 3B, with reference to FIGS. 4 to 6.

First, with reference to FIG. 4, description will be made of a configuration for detecting the toner passage time points using a color displacement sensor 405 corresponding to the color displacement sensor 18 illustrated in FIG. 1. The color displacement sensor 405 is disposed so as to face an intermediate transferring belt 407 corresponding to the intermediate transferring belt 6 illustrated in FIG. 1. The color displacement sensor 405 is used for detecting the passage time points of multiple color (black, magenta, cyan and yellow) toners 401 to 404 at which the respective toners pass a toner passage detection position 406 that is an area on the intermediate transferring belt 407 to which a detection light from a light source (not illustrated) is projected.

The multiple color toners 401 to 404 are formed (transferred) at mutually different positions (image-carrying positions) on the intermediate transferring belt 407. When there is not any color displacement, an interval between the toners 401 to 404 is fixed, that is, a predetermined interval.

A detection signal as an output signal from the color displacement sensor 405 changes at each time when the black toner 401, the magenta toner 402, the cyan toner 403 and the yellow toner 404 carried by the intermediate transferring belt 407 sequentially pass the toner passage detection position 406.

A calculator 408 as an acquirer provided in the engine controller 17 illustrated in FIG. 1 acquires, using its internal timer in response to changes of the detection signal from (that is, output changes of) the color displacement sensor 405, the passage time points of the multiple color toners 401 to 404. Furthermore, the calculator 408 calculates, using the passage time point of the black toner (reference color toner) 401 as a reference time point, color displacement amounts between the reference time point and the magenta, cyan and yellow toners as comparative color toners. A method of calculating the color displacement amounts will be described later.

Figure 5A:
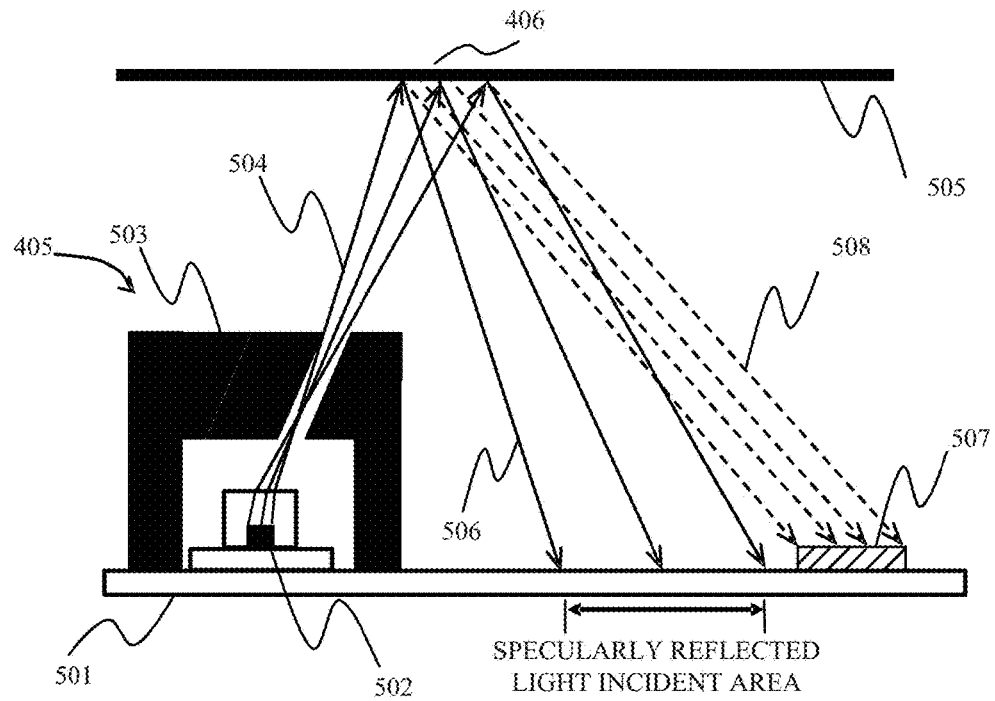
FIGS. 5A and 5B illustrate a configuration of a color displacement sensor in Embodiment 1.
Figure 5B:
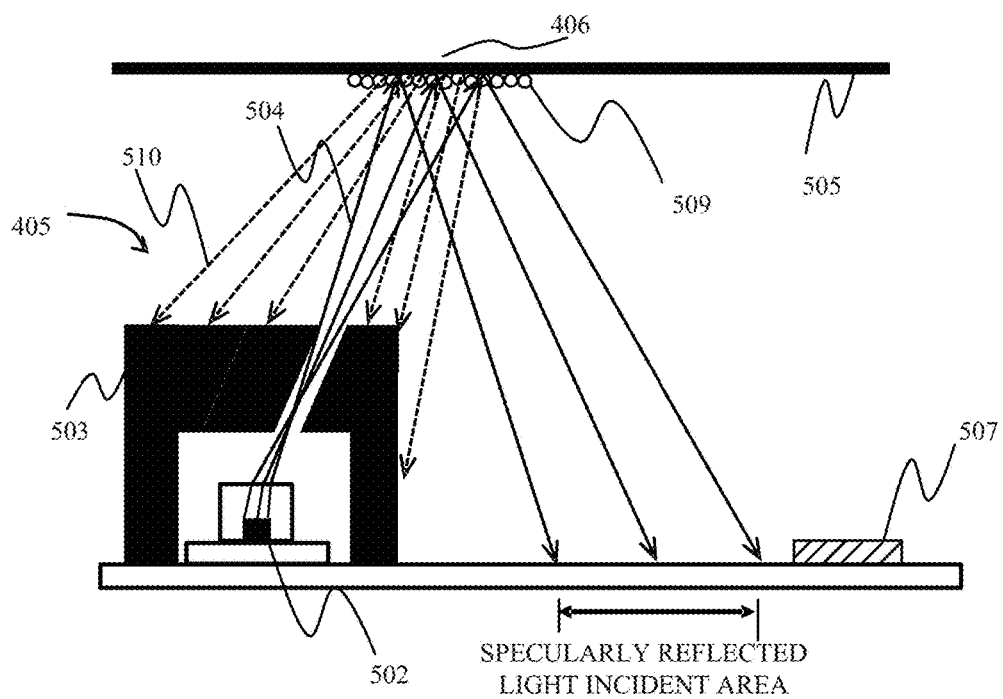

FIGS. 5A and 5B illustrate a configuration example of the color displacement sensor 405 and progressions of the diffusely reflected light in a case where the non-transferred area or the toner on the intermediate transferring belt 505 is located at the toner passage detection position 406. FIG. 5A illustrates the case where the non-transferred area on the intermediate transferring belt 505 is located at the toner passage detection position 406.

A light flux 504 emitted from a light source 502 mounted on a substrate 501 is projected to the intermediate transferring belt 6 through a waveguide member 503 that is provided on the same substrate 501 and gives directivity to the light flux 504. A specularly reflected light flux 506 reflected by the non-transferred area on the intermediate transferring belt 505 reaches a specularly reflected light incident area on the substrate 501.

A light detector (light receiver) 507 is provided in an area different from the specularly reflected light incident on the substrate 501. The light detector 507 receives a diffusely reflected light (forward scattering light) 508 progressing to a specular reflection direction (that is, forward) from the intermediate transferring belt 505 to output the detection signal whose value corresponds to its received light amount.

FIG. 5B illustrates the case where a polymerized toner 509 is located at the toner passage detection position 406. The light flux 504 projected to the polymerized toner 509 from the light source 502 is diffused toward the light source 502 (that is, backward) mainly as a backward scattering light flux 510. Therefore, the diffusely reflected light amount to the specular reflection direction is attenuated, and thereby the signal value of the detection signal from the light detector 507 is lowered as compared with the case illustrated in FIG. 5A. The calculator 408 acquires a time point when the signal value of the detection signal is lowered (that is, the output change of the light detector 507 is generated) as the toner passage time point.

Although the diffusely reflected lights from the mutually different color toners 401 to 404 have differences in light amounts, their directivities are mutually common as long as they are the polymerized toners 509. Therefore, the color toners 401 to 404 have similar effects of attenuating the diffusely reflected light amount from the intermediate transferring belt 505 regardless of their colors.

As described above, this embodiment detects the attenuation of the diffusely reflected light amount from the intermediate transferring belt 505 by utilizing that the intermediate transferring belt 505 and the toner 509 have mutually opposite scattering directivities, which enables acquiring (detecting) the passage time points of all the multiple color toners. Accordingly, this embodiment enables accurately acquiring the toner passage time points without being influenced by the configuration of the color displacement sensor and by the change in light ray angle of the reflected light, regardless of whether the toner's color is a chromatic color or an achromatic color.

Figure 6A:
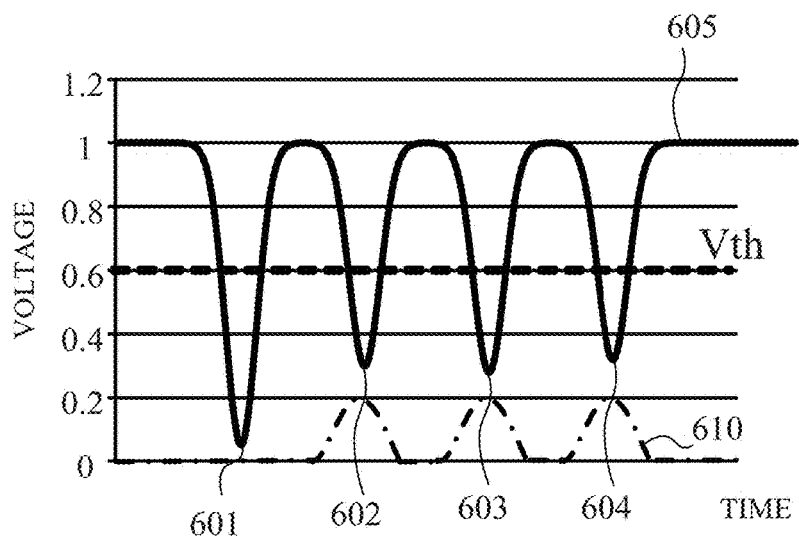
FIGS. 6A and 6B illustrate toner passage times detected by the color displacement sensor in Embodiment 1.
Figure 6B:
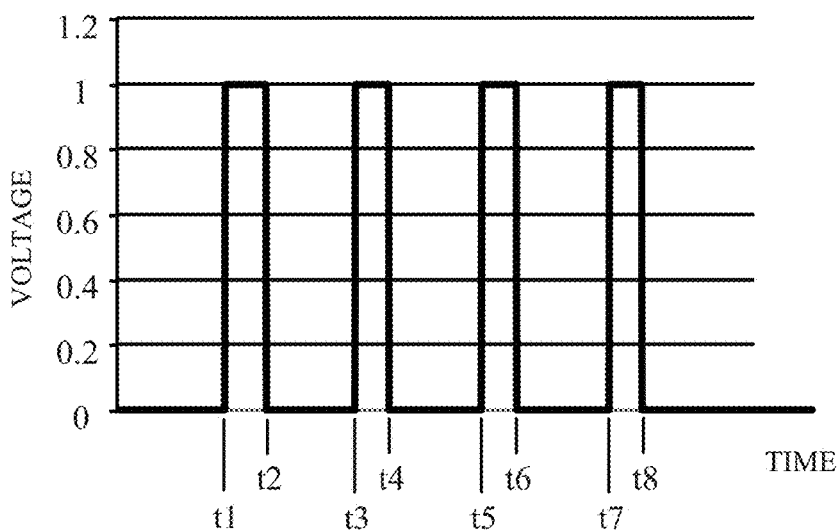

With reference to FIGS. 6A and 6B, description will be made of a method of acquiring the toner passage time points in this embodiment. FIG. 6A illustrates, by a solid line, a detected voltage value as the signal value of the detection signal output from the color displacement sensor 405 (that is, the light detector 507) in response to the passage of each color toner through the toner passage detection position.

Four minimal values 601 to 604 of the detected voltage value correspond to the attenuations off the diffusely reflected light amount in response to the passage of the four color (black to yellow) toners 401 to 404 illustrated in FIG. 4. A high level 605 of the detected voltage value indicates a detected voltage value when the color displacement sensor 405 receives the diffusely reflected light from the non-transferred area on the intermediate transferring belt 505. Furthermore, a dashed-dotted line in FIG. 6A indicates a detected voltage value 610 corresponding to the diffusely reflected light amount when assuming that the light detector 507 receives the diffusely reflected light form each color toner.

As understood from comparison of this detected voltage value 610 with the detected voltage value (601 to 605) in this embodiment, this embodiment acquires the toner passage time points in response to the changes in detected voltage value in a voltage range (output level) higher than the detected voltage value 610 corresponding to the diffusely reflected light from the toner.

FIG. 6B illustrates a binarized voltage value when the detected voltage value illustrated in FIG. 6A is binarized with a threshold Vth. Arrival time points at which the four color toners arrive at the toner passage detection position are respectively indicated by t1, t3, t5 and t7, and passage completion time points at which the passages of the four color toners through the toner passage detection position are completed are respectively indicated by t2, t4, t6 and t8. The toner passage time point of each color toner is calculated as a center time point between its arrival time point and its passage completion time point as indicated by following expressions (1) to (4).

$$Tbk=(t2+t1)/2 \quad (1)$$

$$Tm=(t4+t3)/2 \quad (2)$$

$$Tc=(t6+t5)/2 \quad (3)$$

$$Ty=(t8+t7)/2 \quad (4)$$

In the above expressions, Tbk represents the passage time point of the black toner 401, Tm represents the passage time point of the magenta toner 402, Tc represents the passage time point of the cyan toner 403, Ty represents the passage time point of the yellow toner 404.

Next, description will be made of the method of calculating the color displacement amount depending on the acquired toner passage time point. The calculator 408 that is part of the engine controller 17 as a computer executes a passage time point acquisition process for this calculation, according to a passage time point acquisition process program as a computer program. As described above, the reference color toner is the black toner 401, and the comparative color toner is the magenta toner 402. An ideal difference between the toner passage time points when there is no color displacement between the four color toners, that is, these toners are formed at a predetermined interval is represented by (Tm−Tbk)ideal. On the other hand, the difference between the actually acquired toner passage time points is represented by (Tm−Tbk)real.

When (Tm−Tbk)real is different from (Tm−Tbk)ideal as expressed by following expression (5), that is, the difference ΔT therebetween is not 0, a color displacement amount ΔT as a time (color displacement time) exists.

$$\Delta T = (Tm-Tbk)\text{ideal} - (Tm-Tbk)\text{real}(\neq 0) \quad (5)$$

The calculator 408 feeds back the color displacement amount ΔT as, for example, a correction value for correcting a time of forming the electrostatic latent image on the photoconductive drum. This enables correcting the position at which the comparative color toner is formed on the intermediate transferring belt, and thereby enables reducing the color displacement.

This embodiment described the case where, in the color displacement sensor 405 illustrated in FIGS. 5A and 5B, the light detector 507 is disposed on an opposite side to the light source 502 across the specularly reflected light incident area. However, the light detector may be disposed at other positions depending on an optical path property from the light source and on diffuse reflection properties of the intermediate transferring belt and the toner for the optical path property. The light detector may be disposed at a position where the diffusively reflected light amount (received light amount) from the non-transferred area on the intermediate transferring belt is larger than that from the toner. As long as this condition is satisfied, the light detector may be disposed on the same side as that of the light source 502 with respect to the specularly reflected light incident area.

Embodiment 2

A second embodiment (Embodiment 2) will describe a case where both the intermediate transferring belt 6 and the toner (grinded toner) have the perfect diffusion property. A configuration of detecting the toner passage time points in this embodiment is identical to that described with reference to FIG. 4.

Figure 7:
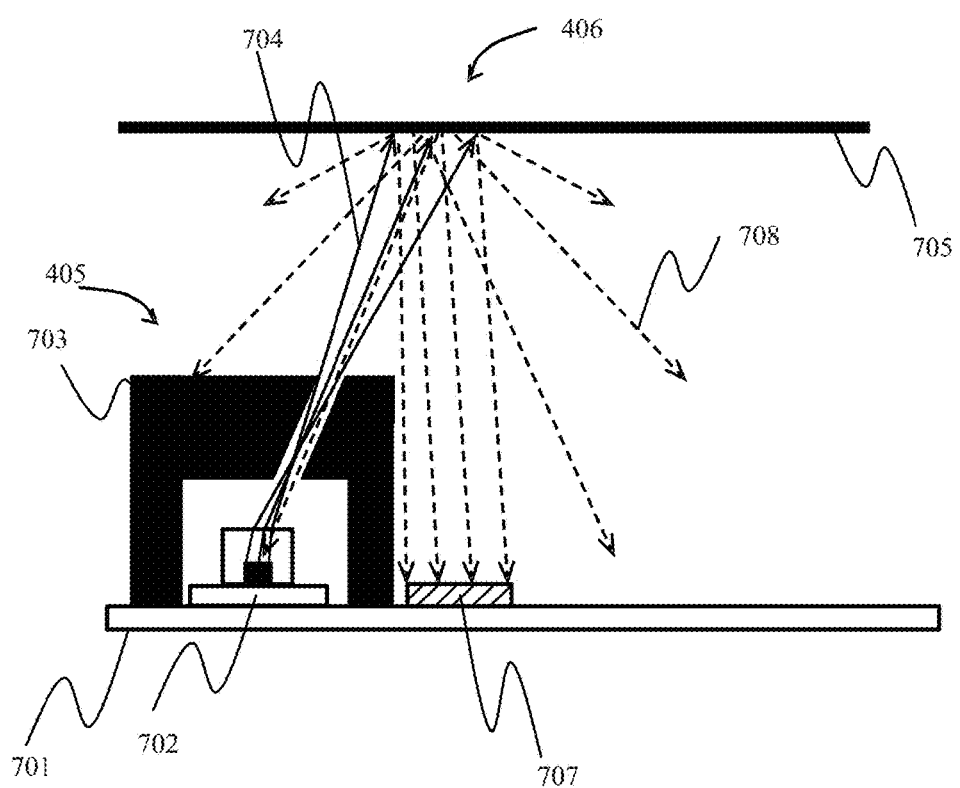
FIG. 7 illustrates a configuration of a color displacement sensor in Embodiment 2.

FIG. 7 illustrates a configuration example of the color displacement sensor 405 and progressions of a diffusely reflected light 708 when the non-transferred area of an intermediate transferring belt 705 corresponding to the intermediate transferring belt 6 in illustrated FIG. 1 is located at the toner passage detection position 406.

A light flux 704 emitted from a light source 702 mounted on a substrate 701 is projected to the intermediate transferring belt 705 through a waveguide member 703 that is provided on the same substrate 701 and provides a directivity to the light flux 704. Part of a diffusely reflected light 708 approximately perfectly diffusely reflected at the non-transferred area on the intermediate transferring belt 705 is received by a light detector (light receiver) 707 provided on the substrate 701. The light detector 707 outputs a detection signal whose signal value corresponds to its received light amount. A diffusely reflected light when the grinded toner is located at the toner passage detection position 406 is similar to the above diffusely reflected light.

In order to successfully detect the passage of the grinded toner, an additive amount of the carbon black dispersed in the base layer of the intermediate transferring belt 705 is adjusted as described with reference to FIG. 2B such that the light detector 707 can receive a larger amount of the diffusively reflected light from the intermediate transferring belt 705 than that from the grinded toner.

Thus, in response to the passage of all the color toners, a detected voltage value similar to the detected voltage value (601 to 605) as illustrated in FIG. 6A can be acquired. This embodiment also acquires the toner passage time points in response to the changes in detected voltage value from the color displacement sensor 405 in a voltage range (output level) higher than the detected voltage value corresponding to the diffusely reflected light from the toner. Accordingly, this embodiment enables accurately acquiring the toner passage time points without being influenced by the configuration of the color displacement sensor and by the change in light ray angle of the reflected light, regardless of whether the toner's color is a chromatic color or an achromatic color. A method of calculating the color displacement amount depending on the acquired toner passage time points is the same as that described in Embodiment 1.

Although Embodiments 1 and 2 described the case of providing, using the waveguide member 503 or 703, the directivity to the light flux from the light source of the color displacement sensor to the intermediate transferring belt, a configuration may be employed which provides a waveguide member to the light detector such that only the diffusely reflected light is received by the light detector.

Embodiment 1 described the configuration of the color displacement sensor for the case where the light diffusion properties of the intermediate transferring belt and the toner have directivities. Furthermore, Embodiment 2 described the configuration of the color displacement sensor for the case where the light diffusion properties of the intermediate transferring belt and the toner have no directivity. However, other cases may be employed. For example, combinations of the intermediate transferring belt and the toner are not limited as long as the intensity of the diffusely reflected light from the intermediate transferring belt in the light detector is higher than that from the toner, and the configuration of the color displacement sensor is also not limited.

Each of the above-described embodiments acquires the passage times of all the color toners, using the diffusely reflected light from the non-transferred area on the intermediate transferring belt. This enables accurately detecting the passage time of each color toner without being influenced by an optical axial displacement between multiple detectors of an optical sensor and by a change in light ray angle of a specularly reflected light from the intermediate transferring belt.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-203609, filed on Oct. 17, 2016, which is hereby incorporated by reference herein in its entirety.

What is claimed is:

1. An image-forming apparatus comprising:
multiple developing units configured to form images using multiple color developers whose colors are mutually different;
an image carrier configured to, in color displacement detection, carry the multiple color developers transferred thereon from the multiple developing units at mutually different image-carrying positions;
an optical sensor configured to project a light to the image carrier and receive a reflected light from the image carrier; and
an acquirer configured to acquire, in response to output from the optical sensor, passage times at which the multiple color developers carried by the image carrier respectively pass a detection position,
wherein the optical sensor is configured to receive a diffusively reflected light from a non-transferred area of the image carrier on which the developers are not transferred,
the acquirer is configured to acquire the passage times of all the multiple color developers, in response to changes in the output from the optical sensor at an output level higher than that corresponding to a diffusively reflected light from the developers on the image carrier, and
the optical sensor includes a light-receiving portion that is provided at a position where the received diffusively reflected light amount from the nontransferred area of the image carrier is larger than that from the developers on the image carrier.

2. An image-forming apparatus according to claim 1, wherein the light-receiving portion is provided in an area different from an area where a specularly reflected light from the image carrier is made incident and that receives the diffusively reflected light from the non-transferred area.

3. An image-forming apparatus according to claim 1, wherein the acquirer is configured to acquire a color displacement amount between the multiple color developers, using the acquired passage times of the multiple color developers.

4. An image-forming apparatus according to claim 1, wherein the image carrier includes a light-diffusive layer.

5. An image-forming apparatus according to claim 1, wherein the image carrier has a light-diffusive surface.

6. A non-transitory storage medium storing a computer program for causing a computer in an image-forming apparatus to execute an acquisition process, the image-forming apparatus including multiple developing units configured to form images using multiple color developers whose colors are mutually different, an image carrier configured to, in color displacement detection, carry the multiple color developers transferred thereon from the multiple developing units at mutually different image-carrying positions, and an optical sensor configured to project a light to the image carrier and receive a reflected light from the image carrier, the acquisition process acquiring, in response to output from the optical sensor, passage times at which the multiple color developers carried by the image carrier respectively pass a detection position, the acquisition process comprising:
a process to acquire output from the optical sensor that receives a diffusively reflected light from a non-transferred area of the image carrier on which the developers are not transferred; and
a process to acquire the passage times of all the multiple color developers, in response to changes in the output from the optical sensor at an output level higher than that corresponding to a diffusively reflected light from the developers on the image carrier,
wherein the received diffusively reflected light amount from the nontransferred area of the image carrier is larger than that from the developers on the image carrier due to a position of a light-receiving portion of the optical sensor.

7. A non-transitory storage medium according to claim 6, wherein a light-receiving portion is provided in an area different from an area where a specularly reflected light from the image carrier is made incident and that receives the diffusively reflected light from the non-transferred area.

8. A non-transitory storage medium according to claim 6, wherein the acquisition process acquires a color displacement amount between the multiple color developers, using the acquired passage times of the multiple color developers.

9. A non-transitory storage medium according to claim 6, wherein the image carrier includes a light-diffusive layer.

10. A non-transitory storage medium according to claim 6, wherein the image carrier has a light-diffusive surface.

* * * * *